United States Patent
Raszillier et al.

(10) Patent No.: US 9,919,471 B2
(45) Date of Patent: Mar. 20, 2018

(54) ULTRASONIC MACHINE TOOL

(71) Applicant: MS Ultraschall Technologie GmbH, Spaichingen (DE)

(72) Inventors: Roland Raszillier, Donaueschingen (DE); Volker Krell, Neuhausen (DE)

(73) Assignee: MS ULTRASCHALL TECHNOLOGIE GMBH, Spaichingen (DE)

( * ) Notice: Subject to any disclaimer, the term of this patent is extended or adjusted under 35 U.S.C. 154(b) by 0 days.

(21) Appl. No.: 15/427,509

(22) Filed: Feb. 8, 2017

(65) Prior Publication Data

US 2017/0232660 A1    Aug. 17, 2017

(30) Foreign Application Priority Data

Feb. 8, 2016    (DE) .................. 10 2016 102 164

(51) Int. Cl.
| | |
|---|---|
| *B32B 37/00* | (2006.01) |
| *B29C 65/08* | (2006.01) |
| *G01N 3/16* | (2006.01) |
| *B29C 65/74* | (2006.01) |
| *B29C 65/00* | (2006.01) |

(52) U.S. Cl.
CPC .............. *B29C 65/08* (2013.01); *B29C 65/74* (2013.01); *B29C 66/9221* (2013.01); *B29C 66/9231* (2013.01); *B29C 66/934* (2013.01); *B29C 66/951* (2013.01); *G01N 3/16* (2013.01); *G01N 2203/0003* (2013.01); *G01N 2203/0017* (2013.01); *G01N 2203/0298* (2013.01)

(58) Field of Classification Search
CPC ..... B29C 65/08; B29C 65/74; B29C 66/9221; B29C 66/9231; B29C 66/932; B29C 66/951; G01N 3/16
USPC .......................................... 156/580.1, 580.2
See application file for complete search history.

(56) References Cited

U.S. PATENT DOCUMENTS

| | | | |
|---|---|---|---|
| 4,373,653 | A | 2/1983 | Salzer et al. |
| 5,269,103 | A | 12/1993 | Nagel et al. |
| 5,726,417 | A | 3/1998 | Claussen et al. |
| 5,788,791 | A | 8/1998 | Grewell |
| 6,435,399 | B2 | 8/2002 | Ikoma |

(Continued)

FOREIGN PATENT DOCUMENTS

| | | |
|---|---|---|
| DE | 3233629 A1 | 3/1983 |
| DE | 9313741 U1 | 1/1995 |

(Continued)

OTHER PUBLICATIONS

German Search Report for related German Application No. DE 102016102164.4; dated Nov. 29, 2016; 2 pages.

(Continued)

*Primary Examiner* — James Sells
(74) *Attorney, Agent, or Firm* — Cantor Colburn LLP

(57) ABSTRACT

An ultrasonic machine tool comprises a stand that can be attached to a base plate. The machine furthermore has a vibration generator by means of which a working member can be driven, wherein the vibration generator is borne by a slide displaceably guided in the longitudinal direction of the stand. The slide is in turn borne by a linear drive attached to the stand. The vibration generator is located in the alignment of the adjustment path of the linear drive.

14 Claims, 3 Drawing Sheets

(56) References Cited

U.S. PATENT DOCUMENTS

Figure 1:
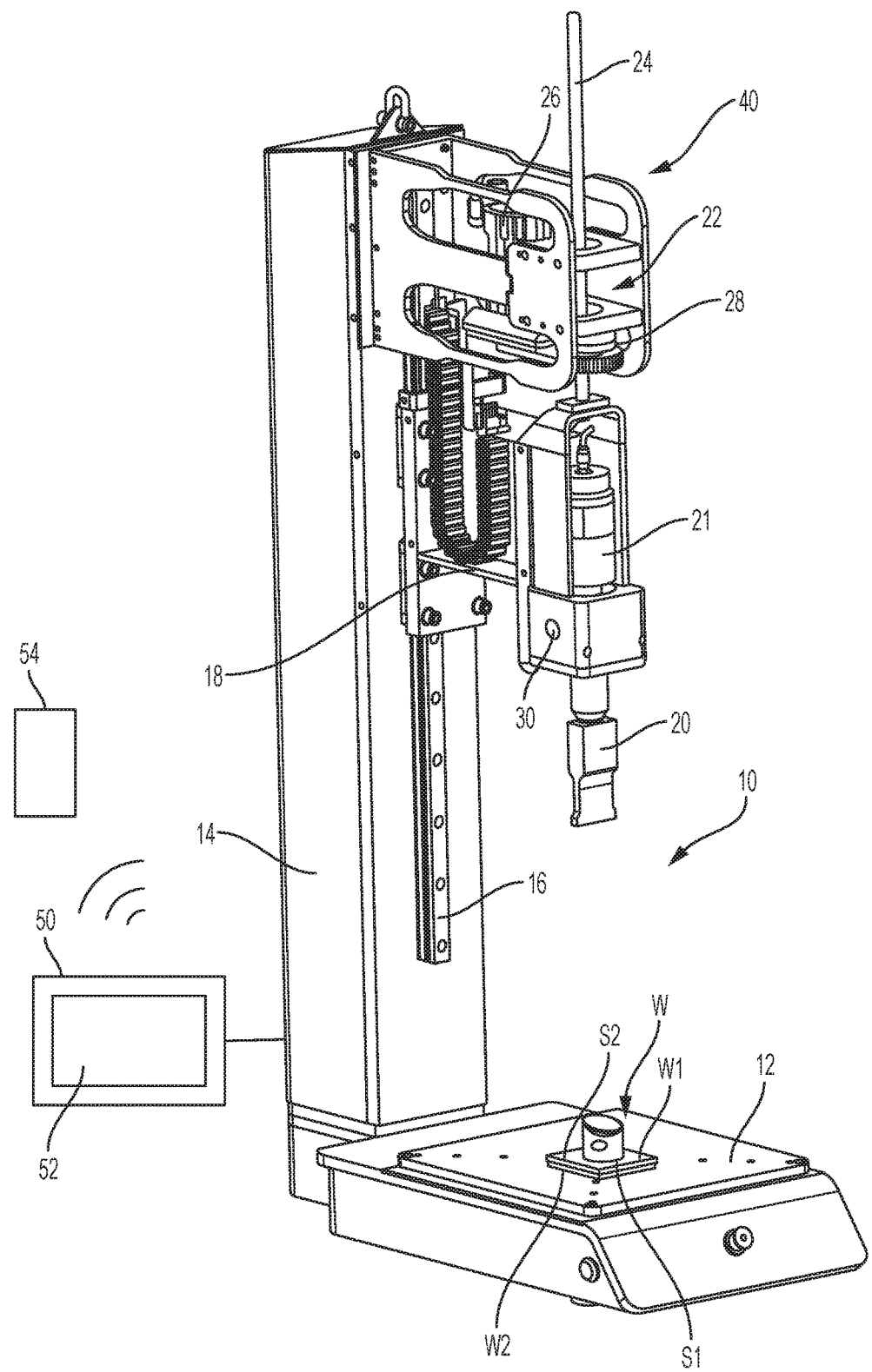

| | | | | |
|---|---|---|---|---|
| 8,052,816 | B2* | 11/2011 | Klinstein | B29C 65/08 |
| | | | | 156/64 |
| 2009/0133803 | A1* | 5/2009 | Lehto | A61F 13/15707 |
| | | | | 156/73.1 |
| 2013/0306216 | A1* | 11/2013 | Cai | B23K 20/10 |
| | | | | 156/64 |

FOREIGN PATENT DOCUMENTS

| | | |
|---|---|---|
| DE | 19752319 C5 | 5/1998 |
| DE | 102006049624 A1 | 4/2008 |
| DE | 102010006130 A1 | 8/2011 |
| EP | 1310319 A1 | 5/2003 |
| EP | 2905108 A1 | 8/2015 |
| GB | 2260096 A | 4/1993 |
| JP | H04250334 A | 9/1992 |
| JP | H11281566 A | 10/1999 |
| JP | 2001118887 A | 4/2001 |
| JP | 2002210590 A | 7/2002 |

OTHER PUBLICATIONS

German Search Report for related German Application No. DE 17150862.5; dated Nov. 24, 2017; 4 pages.

* cited by examiner

ULTRASONIC MACHINE TOOL

The present invention relates to an ultrasonic machine tool in accordance with the preamble of claim 1 whose sonotrode serving as a working member can be traveled in the longitudinal direction of the stand by means of a linear drive.

Such machine tools can comprise a base plate for receiving a workpiece to be machined by the machine tool and a stand along which the working member is displaceably guided. For this purpose, a slide is provided that is displaceably guided along the longitudinal direction of the stand and that bears a vibration generator with which a sonotrode serving as a work member can be excited to make high-frequency vibrations. If the slide is traveled in the longitudinal direction by means of the linear drive until the sonotrode comes into contact with the workpiece to be welded, a desired welding force can be applied to the workpiece via the sonotrode by means of the linear drive, said welding force having to be set to a specific value in dependence on the application, for which purpose a correspondingly formed force regulation can be provided.

The machine tool is provided for such a force regulation with a control that controls the drive and the vibration generator, wherein the drive of the slide and the vibration generator can be controlled with the aid of a force measuring device and a distance measuring device that are connected to the control such the working member is set against the workpiece with a desired force development and is actuated in so doing. An output device is furthermore provided for outputting operating parameters in order, for example, to be able to output or present the duration of the machining, the energy introduced, the applied welding force, etc.

Plastic components can, for example, be welded to one another using an ultrasonic machine tool of the above-described kind, wherein it is necessary for quality assurance that the welded components are at least examined randomly with respect to the quality of the weld connection. For this purpose, the components are typically clamped into a tensile testing apparatus in which the holding force of the weld connection is checked by means of a tensile test.

It is the underlying object of the invention to further develop an ultrasonic machine tool in accordance with the preamble of claim 1 such that a tensile test of components welded to one another is possible in a very simple manner, inexpensively and in a time-saving manner.

This object is satisfied by the features of claim 1 and in particular in that a reception device provided at the slide is provided into which a first workpiece holder can be inserted. The previously welded workpiece that comprises two components can be fastened to the first component using the first workpiece holder that can be inserted into a reception device. A second workpiece holder is furthermore provided that can be fastened to the base plate or to the stand and with which the second component of the workpiece can be held for the tensile test. It is possible in this manner to attach one of the two workpiece holders to each component after the welding together of the two components of the workpiece such that one component is connected to the slide via the first workpiece holder and the other component is connected to the base place or to the stand via the second workpiece holder such that a tensile test can take place by an exertion of force. The control is configured and adapted in accordance with the invention such that it is possible to switch manually and/or automatically between a machining cycle and a tensile test cycle.

A machining cycle is understood as a work routine in which materials are welded together, are separated and/or are sealed. A tensile test cycle is understood as an operating mode of the machine tool in which the control controls the drive of the slide such that a welded workpiece whose two components are connected to the two workpiece holders can be tensioned, wherein the force-distance development of the force measuring device and of the distance measuring device occurring during tensioning is recorded. A tensile test of the workpiece can take place in this manner by the tensile test cycle and it can be determined and output whether the tensile test satisfies the demands, i.e. whether the previously established weld connection is satisfactory.

Advantageous embodiments of the invention are described in the description, in the drawing and in the dependent claims.

In accordance with a first advantageous embodiment, the workpiece holder can be inserted into the reception device without the working member having to be removed. In this manner, the machine tool can be prepared for a tensile test in a very simple manner after a machining cycle in that the first workpiece holder is inserted into the reception device provided at the slide. The first workpiece holder subsequently only has to be connected to a component of the welded workpiece and the other component has to be coupled to the second workpiece holder fastened to the base plate or to the stand in order to tension the workpiece.

It is generally sufficient if the ultrasonic machine tool together with its stand is positioned relative to a base plate that is in a fixed position, for example relative to an already present work plate or work surface. It can, however, also be advantageous if the stand is provided together with a base plate and is connected to it so that the machine tool is portable.

Not only a separate tensile testing machine can be completely dispensed with using the machine tool in accordance with the invention. It is rather also possible to achieve a simplified quality control by a suitable formation of the control. In accordance with a further advantageous embodiment, the control can thus be configured and adapted such that it automatically switches between a machining cycle and a tensile test cycle in intervals that can be fixed. In this manner, provision can be made in a mandatory manner by the control that a tensile test take place at a desired interval after a machining, i.e. after a welding of two components of a workpiece.

It is possible to fix the length of an interval in accordance with a further advantageous embodiment by the number of workpieces machined after one another. The control can, for example be configured and adapted such that a tensile test generally takes place, for example, after 25 carried out welding processes.

In accordance with a further advantageous embodiment, the length of an interval can be fixable in a randomly controlled manner by the control. A tensile test can thus be provided after a random number of machining cycles or welding processes or after a randomly selected time period. It is also possible that the control is configured and adapted such that ten randomly selected parts per layer are, for example, subjected to a tensile test in that the machine tool switches over to a tensile test cycle after the welding of these parts. The machining of further parts is then only possible when the tensile test of the previously welded part has been carried out.

In accordance with a further advantageous embodiment, the control of the machine tool can have an input device by which the further operating mode of the machine tool can be predefined in dependence on the result of at least one tensile test. The reaction of the machine tool to a (negative) result of a tensile test can hereby be set or selected. The machine tool can, for example, be completely blocked when a specific number of negative tensile tests have been carried out after one another. It can also be predefined as a further operating mode of the machine tool that said machine tool initially continues to work in normal operation until the next error occurs. It is also possible to specify to the control that the negative result of the tensile test is deleted or ignored when no further error has occurred during a tensile test for a specific following time period, for example within three hours.

In accordance with a further advantageous embodiment, the control can be configured and adapted such that an insufficient result of a tensile test is output and that in this case a subsequent predetermined number and order of machining cycles and tensile test cycles that have to be carried out is predefined by the control. For example, a finding can be made via the control on what procedure should be followed in the event of reject parts that have not passed a tensile test. It can, for example, be predefined that two further parts are first welded and checked until a return to normal operation is made.

In accordance with a further advantageous embodiment, the output device of the machine tool can be coupled, in particular wirelessly, to a mobile operating unit. It is possible in this manner to transmit information from the machining and also from the tensile test to a mobile operating unit, for example to a smartphone, with the aid of an app. A decision on how work should continue after a reject part can then subsequently be made by an operator via the smartphone or via another operating unit.

In accordance with a further advantageous embodiment, the machine tool can be blockable by the control in dependence on results of the tensile test. It can be ensured in this manner that no unnecessary reject parts are produced if the result of a tensile test repeatedly turns out negative.

Not only the high costs of an otherwise required tensile test machine can be saved by the machine tool in accordance with the invention. It is rather also possible to make a switch from a machining cycle to a tensile test cycle in a very short time and in a very simple manner. The additional costs for a tensile test are minimal in this respect since all the hardware components are per se already present in the machine tool. Only a corresponding adaptation of the control as well as the first and second workpiece holders that can be coupled to the slide or to the base plate or to the stand additionally have to be provided.

Figure 2:
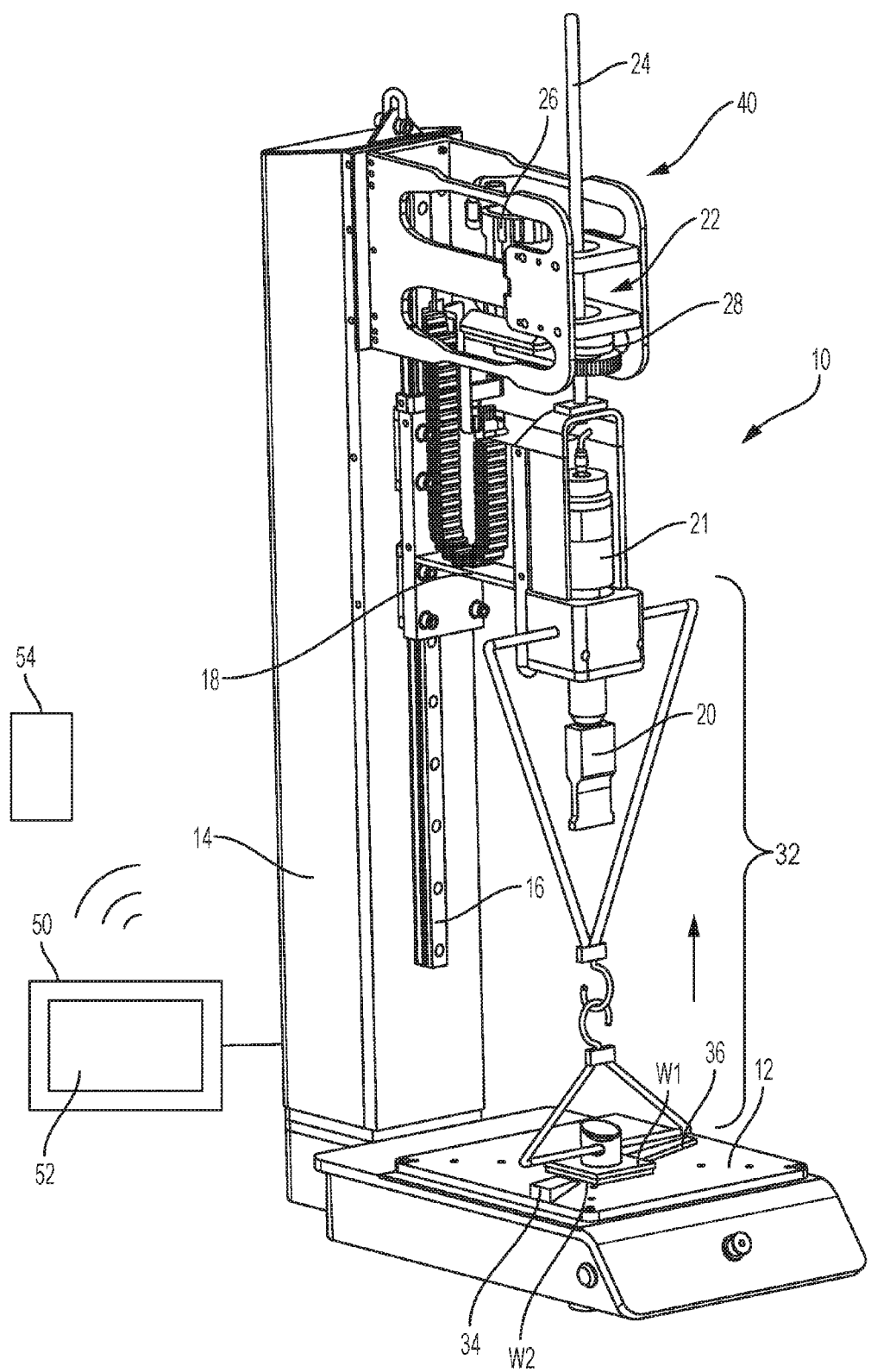
Figure 3:
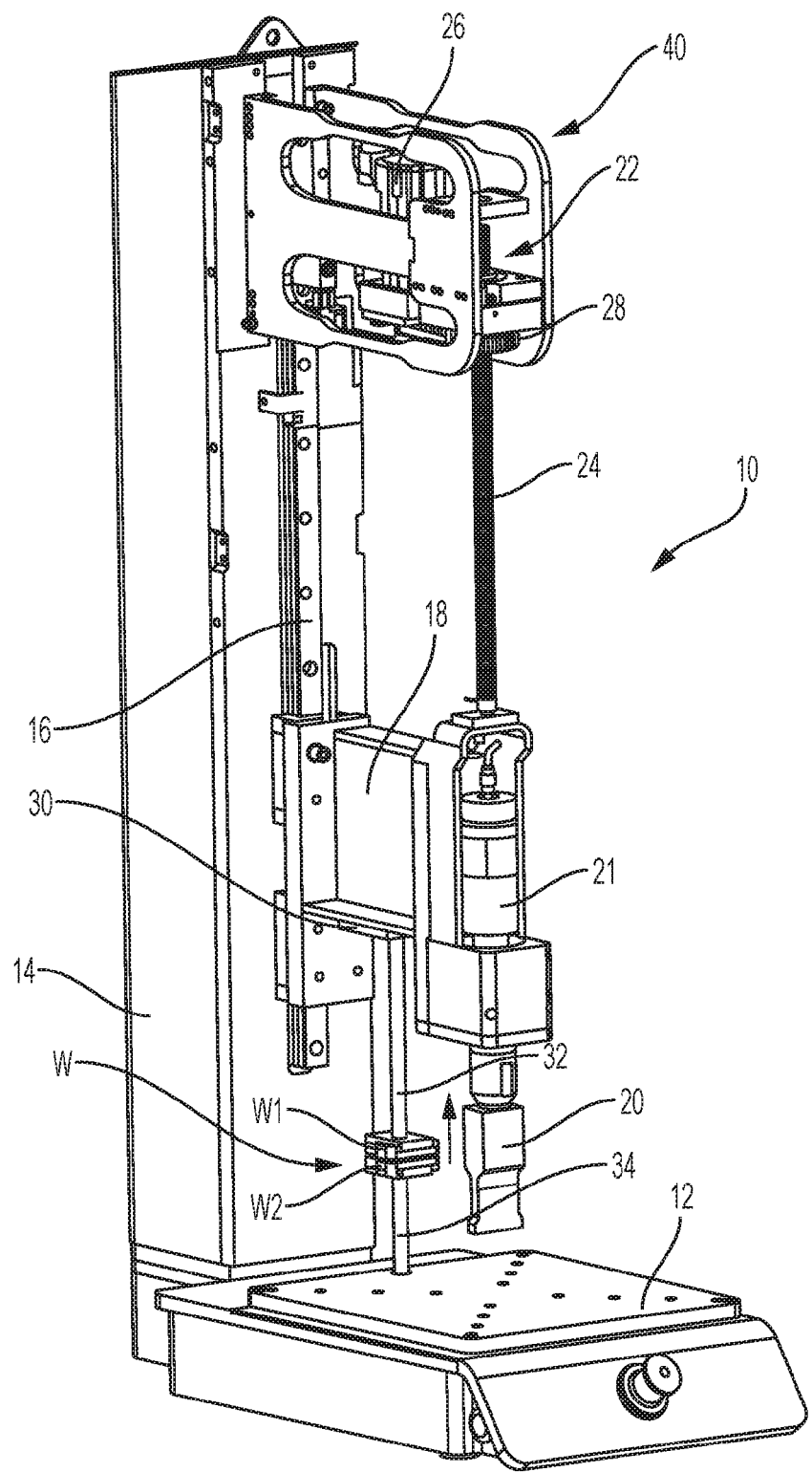

The invention will be explained in the following purely by way of example with reference to the enclosed Figures. There are shown:

FIG. 1 a perspective representation of an ultrasonic machine tool in accordance with the invention during a machining cycle;

FIG. 2 a perspective of the ultrasonic machine tool of FIG. 1 during a tensile test cycle; and FIG. 3 a perspective view of a second embodiment of an ultrasonic machine tool during a tensile test cycle.

The ultrasonic machine tool 10 shown in FIGS. 1 and 2 has a base plate 12 on which a workpiece to be welded is arranged and that is connected in a flexurally rigid manner to an upright stand 14. A guide rail 16 is fastened to the stand 14 along the longitudinal direction of the stand 14 and a frame-like slide 18 is displaceably guided along it that bears a vibration generator 21 with which a sonotrode 20 serving as a working member can be excited to make high-frequency vibrations.

To be able to travel the slide 18 together with the vibration generator 21 and the sonotrode 20 by the guide rail 16 along the stand 14, a linear drive 22 in the form of a spindle drive is provided in the described embodiment whose threaded spindle 24 is attached to the frame-like slide 14 in an upright manner such that the vibration generator 21 is located in the alignment of the adjustment path of the linear drive 22, i.e. in the spindle axis. Other drives are naturally also possible. The linear drive 22, and in particular its spindle nut 28, is supported in the embodiment shown here in the manner in accordance with the invention at a frame-like elastically deformable flexure bearing of steel that is designated as a whole by the reference number 40 and that is in turn attached in a freely projecting manner to the free end of the stand 14.

A servomotor 26 is provided to actuate the linear drive 22 and its output drive gear drives the spindle nut 28 via a belt, with said spindle nut being provided with an external toothed arrangement along its periphery.

A control 50 is provided to control the machine tool for machining cycles and also for tensile test cycles that has an input device and an output device for inputting and for outputting operating parameters, for example in the form of a touchscreen 52. The control is in this respect connected both the drive 22 and to the force measuring device and the distance measuring device as well as to the vibration generator 21. Any desired machining process can be predefined and carried out with the aid of the control by a suitable input of the required operating parameters. The control makes provision during a tensile testing cycle that the slide 18 is moved upward with a predefined force characteristic, with the distance covered by the slide being determined and recorded by the control. The tensile testing processes can thus be recorded, saved, presented and output in data form by the control.

The control 50 is furthermore wirelessly connected to a mobile operating unit 54, for example to a smartphone, by which the machine tool can be controlled by a corresponding app (corresponding application software).

The workpiece W located on the base plate 12 is shown purely schematically in FIG. 1 and comprises a first component W1 that is welded to a second component W2 along two weld lines S1 and S2. To weld the two components, the workpiece W can be fixed in its position on the base plate 12 using fixing elements, not shown, such that a welding can take place along the weld lines S1 and S2 with the aid of the sonotrode 20 by lowering the slide 18.

The spindle nut 28 is driven by means of the servomotor 26 for the welding and the slide 18, including the vibration generator 21 and the sonotrode 20, is lowered until the sonotrode 20 moves into contact with the component W1 of the workpiece located on the base plate 12, whereby a welding force can be applied in the desired manner to the workpiece located on the base plate 12 with the help of the linear drive 22 via the sonotrode 20, which has the result, in particular when the workpiece is comparatively rigid or unyielding, that the frame-like flexure bearing 40 undergoes an elastic deformation in the desired manner.

Since the vibration generator 21 together with its sonotrode 20 is located in accordance with the invention in the alignment of the adjustment path of the linear drive 22, no deformations or only slight deformations occur in the force flow path between the sonotrode 20 and the stand 14 with the exception of this elastic deformation of the elastically deformable flexure bearing 40. Since the working member 20 is also located in the alignment of the adjustment path of the linear drive 22, it is ensured that no uncontrolled bending deformations come about in the region of the linear drive 22 and/or of the vibration generator 21 as a result of a force that is applied to a workpiece that can be positioned on the base plate 12 with the aid of the linear drive 22 via the working member 20. On the other hand, it is deliberately permitted by the flexure bearing 40 that the linear drive 22 can continue its stroke movement within the framework of certain limits from that point in time onward at which the working member 20 comes into contact with the workpiece in order thus to be able to adjust the force applied to the workpiece from the stroke movement occurring from this point in time onward without overshoots occurring.

If a tensile test cycle is to be or must be run through after a machining cycle in which the two components W1 and W2 of the workpiece W have been welded together, the machine tool shown in FIG. 1 can thus be converted in a very simple manner into a tensile test apparatus. For this purpose, a first reception region in the form of two bores 30 (only one bore can be recognized in FIG. 1) is provided in the region of the slide and a first workpiece holder 32 can be inserted into them.

FIG. 2 shows the workpiece holder 32 that is inserted into the reception device 30 and that comprises in the embodiment shown purely by way of example two triangular hoops that are only shown schematically, wherein the upper hoop in FIG. 2 is inserted with two free limbs into the reception device 30 of the machine tool 10. The hoop at the bottom in FIG. 2 is led through a bore in the first component W1 of the workpiece and is coupled to the upper hoop with the aid of two hooks such that the first component W1 can have a force exerted on it with the aid of the drive 22 in the direction of the arrow shown.

The second component W2 of the workpiece W is fixed to the base plate 12 with the aid of two workpiece holders 34 and 36 shown purely schematically such that the workpiece component W2 is fixedly held at the base plate. In this manner, on the exertion of a tensile force on the first workpiece component W1, the previously established weld connection can be tested in that the development of the applied tensile force over the distance is recorded.

As can be recognized from FIG. 2, the first workpiece holder 32 can be inserted in a simple manner into the reception device 30 of the machine tool without the working member 20 in the form of the sonotrode having to be removed.

When running through a tensile test cycle, the drive 22 is controlled by the control 50 such that the former moves the slide 18 upwardly with a predefined tensile force, with the development of the tensile force over the distance being determined and recorded with the aid of the distance measuring device and the force measuring device. If the result satisfies preset demands, a signal is output and/or displayed or stored via the output device 52 or via the operating unit 54, and signals a positive running through of the tensile test. If the tensile test does not satisfy the demands, this is likewise output and/or signaled.

The second embodiment of an ultrasonic machine tool shown in FIG. 3 is formed in the same manner as the embodiment of FIGS. 1 and 2 except for the workpiece holders for the tensile test such that reference can be made to the description with respect to FIGS. 1 and 2 with regard to the general design.

In the ultrasonic machine tool shown in FIG. 3, the workpiece W and the first workpiece holder 32 as well as the second workpiece holder 34 are arranged in a free space that is bounded at the lower side by the base plate 12 at the upper side by the slide 18, at the rear side by the stand 14, and at the front side by the working member 20. Since no machine parts are arranged in this free space, it is suitable for attaching or for accommodating the workpiece holders for the tensile test.

The first workpiece holder 32 for the tensile test, that is in turn only shown purely schematically, is in this embodiment inserted into a reception device 30 that is located at the lower side of the slide 18. A second workpiece holder 34 substantially in alignment with the first workpiece holder is fastened to the base plate 12, but could also be fastened to the stand 14. A workpiece W previously welded together from two components W1 and W2 is arranged between the two workpiece holders 32 and 34 for the tensile test, with the first workpiece holder 32 holding the component W1 and the second workpiece holder holding the component W2. A force can then be exerted in the direction of the arrow onto the workpiece W by actuating the drive 22 such that the strength of the weld connection between the components W1 and W2 can be subjected to a tensile test.

The two workpiece holders 32 and 34 can in the simplest cases be threaded bars whose outer ends are screwed into the reception device 30 or into the base plate 12, with clamping devices for holding the two components being able to be provided at the other ends of the two threaded bars.

It is understood that a control 52 and an operating unit 54 are also provided or can also be provided in the embodiment shown in FIG. 3, such as was described in connection with the embodiment of FIG. 1 and FIG. 2.

In another respect, the control 50 provided in accordance with the invention is configured, as was described in the introduction to the description, such that the control can be switched over between machining cycles and tensile test cycles in accordance with desired criteria.

REFERENCE NUMERAL LIST 10 ultrasonic machine tool
12 base plate
14 stand
16 guide rail
18 frame-like slide
20 working member/sonotrode
21 vibration generator
22 linear drive
24 spindle
26 servomotor
28 spindle nut
30 reception device
32 first workpiece holder
34, 36 second workpiece holder
40 elastically deformable flexure bearing
50 control
52 input and output device
54 operating unit
S1 first weld line
S2 second weld line
W workpiece
W1 first component of the workpiece
W2 second component of the workpiece

The invention claimed is:
1. An ultrasonic machine tool for welding, separating and/or sealing materials, comprising:
a stand that can be positioned relative to a base plate on which a workpiece to be machined can be fixed;

a vibration generator with which a working member can be driven;

a slide that bears the vibration generator and that is displaceably guided in the longitudinal direction of the stand;

a drive for the slide;

a control for controlling the drive and the vibration generator that is connected to a force measuring device and to a distance measurement device;

an output device for outputting operating parameters;

a reception device that is provided at the slide and into which a first workpiece holder can be inserted;

a first workpiece holder that can be inserted into the reception device; and a second workpiece holder that can be fastened to one of the base plate and the stand, wherein the control is configured and adapted such that it is possible to switch manually and/or automatically between a machining cycle and a tensile test cycle.

2. The machine tool in accordance with claim 1, wherein the first workpiece holder can be inserted into the reception device without removing the working member.

3. The machine tool in accordance with claim 1, wherein the stand is connected to the base plate.

4. The machine tool in accordance with claim 1, wherein the control has a speed regulation for the drive.

5. The machine tool in accordance with claim 1, wherein the control is configured and adapted such that it automatically switches over between a machining cycle and a tensile test cycle in fixable intervals.

6. The machine tool in accordance with claim 5, wherein the length of an interval can be fixed by the number of workpieces machined after one another.

7. The machine tool in accordance with claim 5, wherein the length of an interval can be fixed in a randomly controlled manner by the control.

8. The machine tool in accordance with claim 5, wherein the length of an interval can be fixed by the number of workpieces machined after one another; and wherein the length of an interval can be fixed in a randomly controlled manner by the control.

9. The machine tool in accordance with claim 1, wherein the control is configured and adapted such that it switches over into a tensile test cycle after a machining cycle during a machining period for a predetermined number of workpieces.

10. The machine tool in accordance with claim 1, wherein the control has an input device by which the further operating mode of the machine tool can be predefined in dependence on the result of at least one tensile test.

11. The machine tool in accordance with claim 1, wherein the control is configured and adapted such that an insufficient result of a tensile test can be output and such that in this case a subsequent predetermined number and order of machining cycles and tensile test cycles is predefined by the control.

12. The machine tool in accordance with claim 1, wherein the output device can be coupled to a mobile operating unit.

13. The machine tool in accordance with claim 12, wherein the output device can be coupled wirelessly to a mobile operating unit.

14. The machine tool in accordance with claim 1, wherein it is blockable by the control in dependence on results of the tensile test.

* * * * *